United States Patent
Bennett et al.

[11] Patent Number: 6,058,947
[45] Date of Patent: May 9, 2000

[54] CONTAMINATION MONITORING SYSTEM

[75] Inventors: Ryan Paul Bennett; Harry Frank Zaro, Jr.; Naoto Iizuka, all of Vancouver, Wash.

[73] Assignee: SEH America, Inc., Vancouver, Wash.

[21] Appl. No.: 09/169,090

[22] Filed: Oct. 8, 1998

Related U.S. Application Data

[63] Continuation of application No. 08/995,775, Dec. 22, 1997, Pat. No. 5,849,103.

[51] Int. Cl.[7] .............................. B08B 3/06; B08B 13/00
[52] U.S. Cl. .......................................... 134/113; 186/902
[58] Field of Search ................................. 134/151, 155, 134/166 R, 167 R, 186, 200, 902, 113, 66; 73/863.31, 864.31, 863.83, 863.33

[56] References Cited

U.S. PATENT DOCUMENTS

| | | | |
|---|---|---|---|
| 4,027,686 | 6/1977 | Shortes et al. | 134/33 |
| 4,778,532 | 10/1988 | McConnell et al. . | |
| 4,872,356 | 10/1989 | Barnett et al. . | |
| 4,924,890 | 5/1990 | Giles et al. | 134/61 |
| 4,955,402 | 9/1990 | Miranda | 134/107 |
| 5,069,235 | 12/1991 | Vetter et al. . | |
| 5,162,233 | 11/1992 | Komori et al. . | |
| 5,224,503 | 7/1993 | Thompson et al. | 134/95.2 |
| 5,236,515 | 8/1993 | Ueno et al. | 134/25.4 |
| 5,265,632 | 11/1993 | Nishi | 134/133 |
| 5,299,584 | 4/1994 | Miyazaki et al. | 134/56 R |
| 5,331,840 | 7/1994 | Williams | 73/19.1 |
| 5,339,844 | 8/1994 | Stanford, Jr. | 134/107 |
| 5,396,178 | 3/1995 | Rybarski | 324/439 |
| 5,401,212 | 3/1995 | Marvell et al. . | |
| 5,401,328 | 3/1995 | Schmitz | 134/58 R |
| 5,537,202 | 7/1996 | Komatsu et al. | 356/36 |
| 5,647,386 | 7/1997 | Kaiser | 134/113 |
| 5,656,097 | 8/1997 | Oleson et al. . | |
| 5,660,585 | 8/1997 | Swoboda et al. | 454/187 |

FOREIGN PATENT DOCUMENTS

| | | | |
|---|---|---|---|
| 61-160941 | 12/1992 | Japan | 134/902 |
| 5-152273 | 6/1993 | Japan | 134/902 |

OTHER PUBLICATIONS

"Creative Engineering and Ultra–Trace Analysis of Ultra Pure Process Media," Fabry et al., 1996 Semiconductor Pure Water and Chemicals Conference, Mar. 4–7, 1996 Santa Clara Convention Center, Santa Clara, California, UPW & Chemical Proceedings, pp. 1–24.

Primary Examiner—Philip R. Coe
Attorney, Agent, or Firm—Kolisch, Hartwell, Dickinson, McCormack & Heuser

[57] ABSTRACT

A contamination monitoring system having a portable framework which carries a rinsing bath for detachable connection to a remote fluid source. A transport structure is mounted on the framework to accommodate transport of the system to and from the remote fluid source. The framework includes a chamber which encloses the rinsing bath to isolate it from the surrounding environment, typically using a filter which removes unwanted particles from air within the chamber. The filter also typically creates a vertical airflow within the chamber. In one embodiment, the system employs a rinsing bath with inner and outer tanks, the inner tank being configured to hold wafers to be rinsed and the outer tank being configured to hold the inner tank. An input port introduces fluid from the remote fluid source into the inner tank for overflow into the outer tank. The outer tank employs an output port for discharge of fluid received from the inner tank. The system identifies contaminated fluid using a test wafer which is cleansed within the rinsing bath and compared to a wafer having optimal characteristics. The source of contamination may be identified by connecting the rinsing bath to various outputs along the fluid path from the remote fluid source, which effectively allows the user to identify an affected fluid path segment.

15 Claims, 2 Drawing Sheets

CONTAMINATION MONITORING SYSTEM

This is a continuation of application Ser. No. 08/995,775, filed Dec. 22, 1997, and now U.S. Pat. No. 5,849,103.

TECHNICAL FIELD

The present invention relates generally to a system for monitoring contamination of fluid used to rinse crystal wafers, and more particularly, to a system employing methodology whereby a source of contamination of fluid received from a remote fluid source may be identified.

BACKGROUND

The production of crystal wafers typically involves cleaning a wafer with an alkali or acid solution, and then rinsing the wafer with purified water so as to remove the solution and any contaminants which have found their way onto the wafer. This cleansing heretofore has involved a series of tanks, each of which is flushed with purified water which rinses any wafer (or wafers) contained within the tank. In such a system, wafers are moved from one tank to the next, each successive tank being configured to further cleanse the wafers of any residual solution or contaminants.

Unfortunately, known wafer rinsing systems do not ensure that the water for rinsing the crystal wafers is adequately purified, and thus do not ensure that resultant crystal wafers are free from defects. Accordingly, it would be useful to provide a system whereby water used to rinse the wafers may be monitored to identify any contamination of the supplied water, and if such contamination does exist, to identify the location of the contamination source.

DISCLOSURE OF THE INVENTION

The aforementioned goals and objectives are met by providing a contamination monitoring system having a portable framework which carries a rinsing bath for detachable connection to a remote fluid source. The rinsing bath includes an input port which detachably connects to the remote fluid source to receive fluid for passage over the crystal wafers contained within the rinsing bath. A transport structure is mounted on the framework to accommodate transport of the system to and from the remote fluid source.

The framework includes a chamber which encloses the rinsing bath to isolate it from the surrounding environment, typically using a filter which removes unwanted particles from air within the chamber. The filter also typically creates a vertical airflow within the chamber.

In one embodiment, the system employs a rinsing bath with inner and outer tanks, the inner tank being configured to hold wafers to be rinsed and the outer tank being configured to hold the inner tank. The input port introduces fluid from the remote fluid source into the inner tank for overflow into the outer tank. The outer tank employs an output port for discharge of fluid received from the inner tank.

The system identifies contaminated fluid using a test wafer which is cleansed within the rinsing bath and compared to a wafer having optimal characteristics. As will be understood, this is accomplished by a method involving the steps of (1) placing a test wafer in a rinsing bath; (2) connecting the input port of the rinsing bath to an output of the remote fluid source; (3) passing fluid from the remote fluid source to the rinsing bath through the input port; (4) removing the test wafer from the rinsing bath; and (5) comparing the removed test wafer to an optimal wafer, a predetermined difference between the test wafer and the optimal wafer being indicative of contamination of the remote fluid source.

Furthermore, the source of contamination may be identified by connecting the rinsing bath to various outputs along the fluid path from the remote fluid source, and repeating the passing, removing and comparing steps upon connection to each output. This effectively allows the user to identify an affected fluid path segment.

These and other objects and advantages of the present invention will be more readily understood after a consideration of the drawings and the detailed description of the preferred embodiment which follows.

DETAILED DESCRIPTION OF THE PREFERRED EMBODIMENT AND BEST MODE OF CARRYING OUT THE INVENTION

Figure 1:
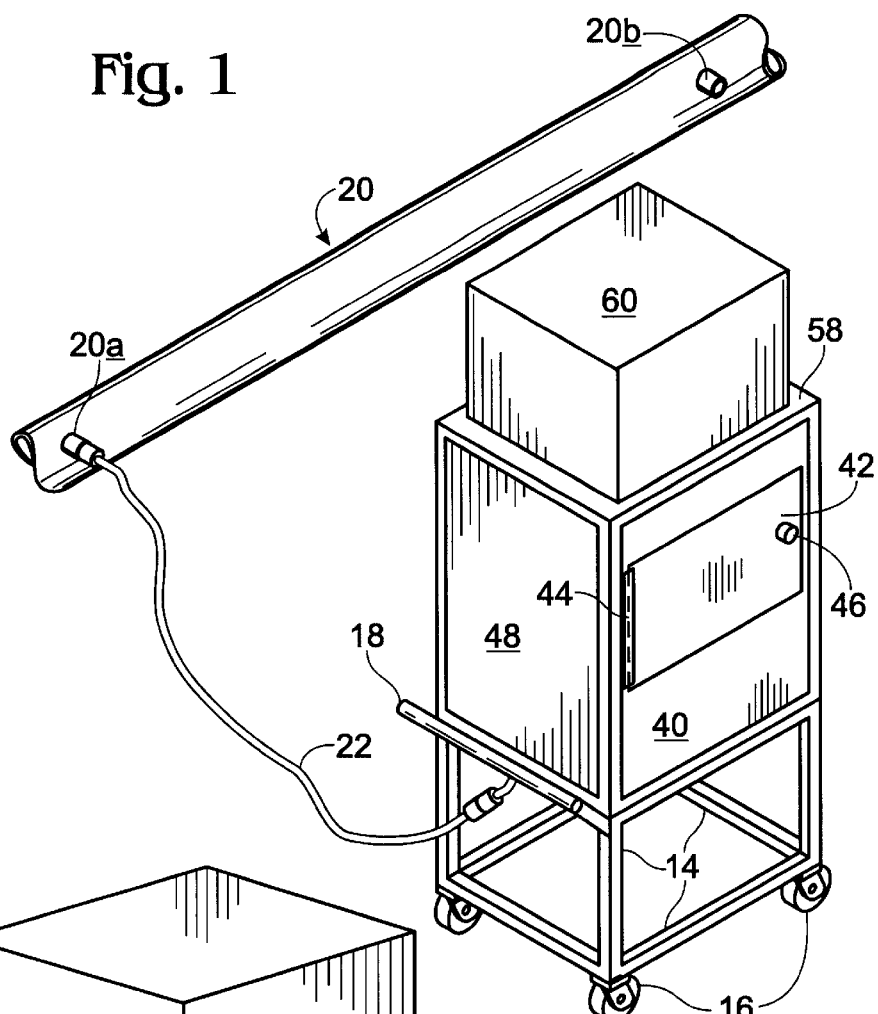
FIG. 1 is an isometric view of a contamination monitoring system constructed in accordance with the present invention, the monitoring system being used in connection with a remote fluid source with one or more fluid outputs.
Figure 2:
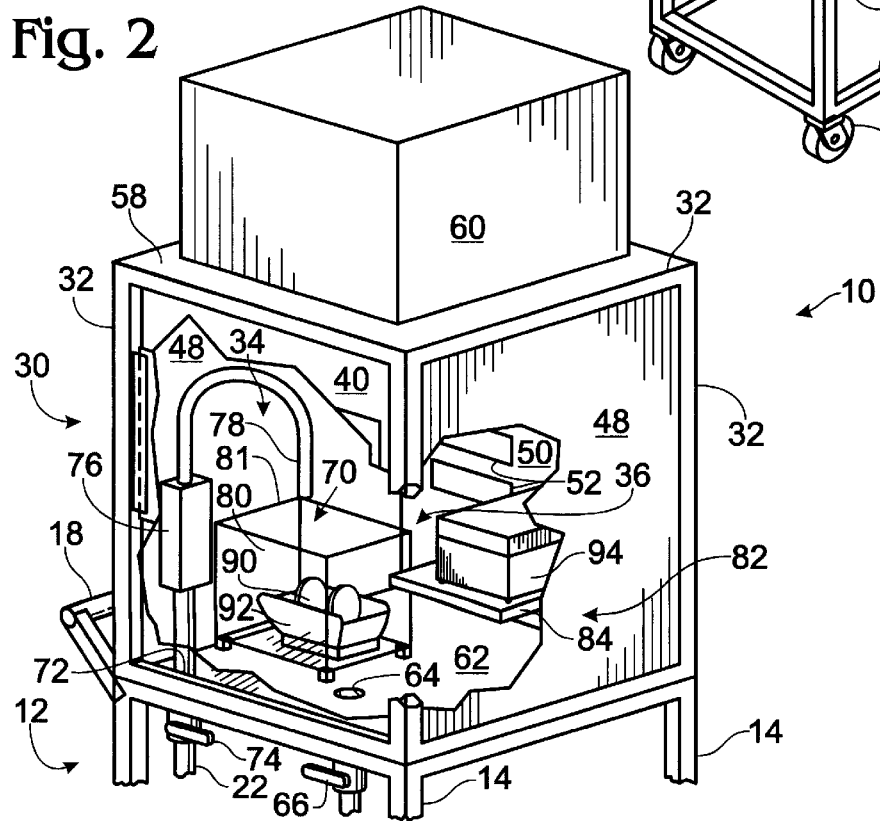
FIG. 2 is a fragmentary isometric view of the wafer rinsing cart shown in FIG. 1, a portal being opened to expose a rinsing bath wherein wafers are cleansed.
Figure 3:
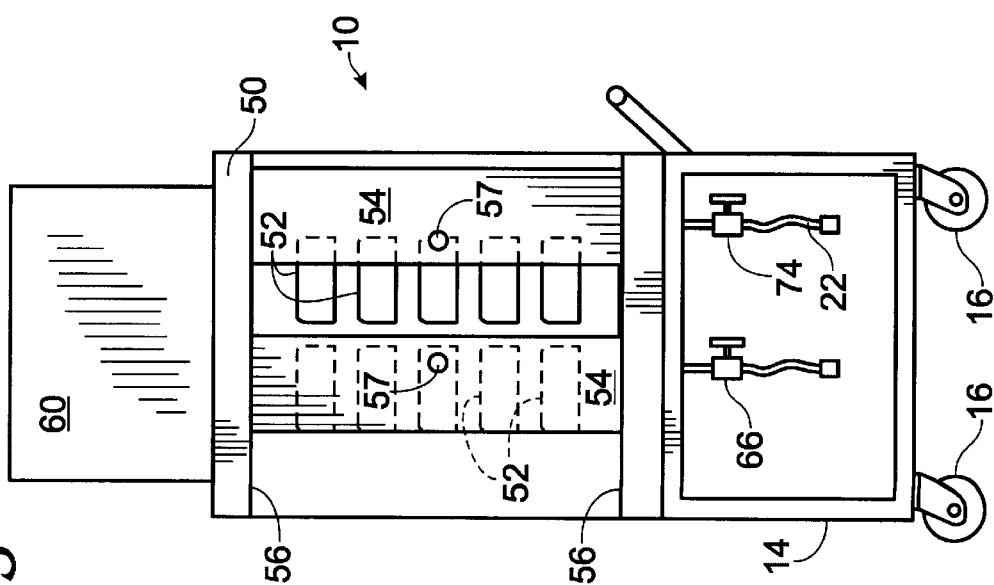
FIG. 3 is a rear view of the wafer rinsing cart shown in FIG. 1.

FIGS. 1 through 3 depict a contamination monitoring system in the form of a cart 10 configured for use in rinsing wafers with fluid (e.g., purified water) received from a remote fluid source 20. As indicated, the fluid typically is supplied to the cart using a hose 22, the hose being configured to connect to any of various outputs (20a, 20b) along a fluid path of the remote fluid source. Although only two outputs are shown, those skilled will recognize that the fluid path may take the form of an elongate conduit with multiple fluid segments extending through various areas of a manufacturing or testing facility.

Cart 10 includes a transport structure 12 which allows cart 10 to be easily transportable to any of the various outputs (20a, 20b), the transport structure typically taking the form of a wheeled lower framework. In the depicted embodiment, the lower framework includes a plurality of frame members 14 assembled such that transport structure 12 has a generally rectangular shape. Wheels 16 are mounted at the base of the transport structure. A handle 18 is attached to the transport structure to allow an operator to maneuver cart 10 to a desired location.

Mounted atop transport structure 12 is a generally rectangular upper framework 30 which is constructed from a plurality of frame members 32. Frame members 14 and 32 are typically made of stainless steel hollow tubing, but may be formed from any suitably strong material flee from contamination. Frame members 14 and 32 are welded or otherwise attached to each other.

Upper framework 30 also includes a chamber 34 defined by front wall 40, side walls 48, rear wall 50, top 58 and bottom 62, all of which are attached to upper framework 30 and preferably made of polypropylene. Chamber 34 encloses a workspace 36 and isolates workspace 36 from the environment in which cart 10 is located. Front wall 40 has a front door 42 mounted on hinges 44. An operator opens and closes front door 42 using a handle 46. Front wall 40 and front door 42 preferably are transparent. Rear wall 50 has a plurality of vents 52. Vent doors 54 slide horizontally on tracks 56 and can be opened and closed to regulate the amount of purified air flowing outwardly through vents 52. An operator opens and closes vent doors 54 using handles 57.

An air filter 60, preferably a HEPA filter, is mounted on top 58 in fluid communication with chamber 34. When filter 60 is running properly and vent doors 54 are opened, purified air is forced into workspace 36 and out vents 52. This constant vertically downward flow of purified air creates a clean area in workspace 36 wherein wafer cleansing and testing for contaminants can be performed. Filter 60 can be of any type known in the semiconductor manufacturing industry and will not be further described.

A rinsing bath 70 is defined within workspace 36, the rinsing bath being configured for selected receipt of purified water via a water inlet 72. The water inlet extends through one of side walls 48 or bottom 62 and includes a valve 74 for selectively allowing water to enter workspace 36. A flow meter 76 is connected, on one side, to valve 74 which regulates the water flow into workspace 36. The other side of flow meter 76 is connected to a spout 78 which directs water into an inner tank 80, which preferably is made of quartz and has an open top 81. Fluid may be fed to inner tank 80 either from above or from below, and is configured so as not to disturb the contents of the inner tank. As indicated, the inner tank is disposed within chamber 34, which defines an outer tank 82. An outlet 64 is defined in bottom 62 and is adapted to drain fluid from the outer tank. A valve 66 selectively opens and closes outlet 64. A shelf 84 is situated within the workspace at an elevation above inner tank 80. The typical shelf has a plurality of perforations (not shown) which contribute to flow of air within the workspace.

The wafer rinsing process will now be described. Cart 10 is moved via transport structure 12 to a selected output of remote fluid source 20. Hose 22, communicating with an output such as 20a, is connected to inlet 72. Valve 74 is opened so that fluid flows through valve 74 which regulates via flow meter 76. Fluid flows out of spout 78 into inner tank 80. When fluid fills inner tank 80, the fluid flows out over open top 81 and into outer tank 82. The fluid is drained from outer tank 82 through outlet 64.

Once the inner tank is filled, an operator opens front door 42 and places one or more crystal wafers such as test wafer 90 into inner tank 80. The test wafer 90 is enclosed in a teflon cassette 92. When test wafer 90 is fully rinsed (as determined by duration of rinse time, or by quantity of fluid flow), the cassette is placed in a sealable box 94 for transport to a testing site. The wafer then is removed from the inner tank for testing to determine the purity level of the fluid. This can be done by comparing the characteristics of test wafer 90 to an optimal wafer (e.g., a wafer which is known to have been rinsed in uncontaminated water). The difference between the two wafers indicates the level of contamination of remote fluid source 20 at output 20a. Suitable wafer quality tests useable with the present invention include vapor phase decomposition, minority carrier recombination lifetime, TXRF, and SIMS, all of which are known in the industry. Valve 66 is then opened so that fluid is drained out of outer tank 82 through outlet 64. Inlet 72 is disconnected from output 20a, and cart 10 can be moved to another output (e.g., 20b) to repeat the wafer rinsing process as desired. Using this repetitive testing, it is possible to identify the source of contamination within the flow path by identifying the point at which contamination of the test water is eliminated.

Figure 4:
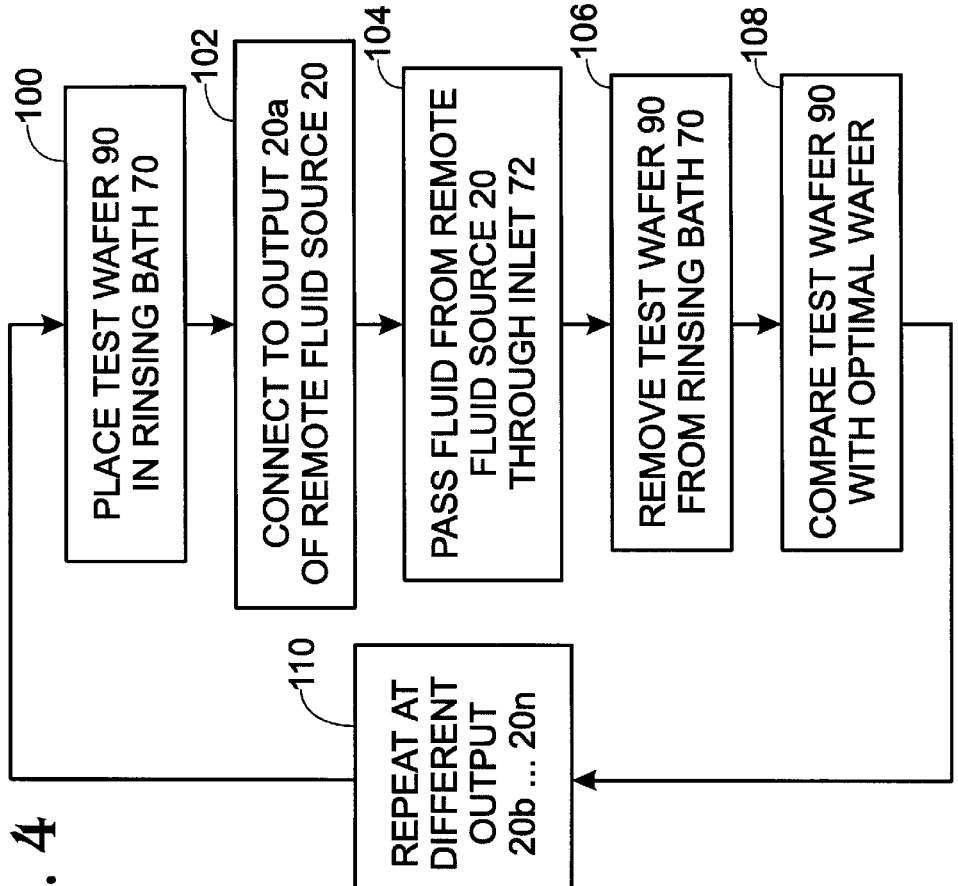
FIG. 4 is a flowchart showing a method of identifying contamination of fluid received from a remote fluid source for use in rinsing crystal wafers.

A method of identifying contaminated fluid using a test wafer according to the present invention is shown in flow-chart form in FIG. 4. In step 100, test wafer 90 is placed in rinsing bath 70. In step 102, inlet 72 is connected to an output port 20a of remote fluid source 20. In step 104, fluid is passed from remote fluid source 20, through inlet 72, to rinsing bath 70. In step 106, test wafer 90 is removed from rinsing bath 70. In step 108, test wafer 90 is compared to an optimal wafer, in which a predetermined difference in characteristics between test wafer 90 and the optimal wafer being indicative of contamination of the remote fluid source. Such characteristics may include, for example, electrical characteristics, chemical characteristics, or the like. If desired, the process can be repeated at different outputs (e.g., 20b, . . . 20n) as shown by step 110.

As demonstrated in the above description, the present invention provides a contamination monitoring system useable in any environment. Filter 60 forces air through vents 52 and ensures a purified airflow within workspace 36. When an operator opens front door 42, workspace 36 remains substantially contaminant-free due to the purified airflow regardless of the contamination level of the surrounding environment.

The wafer comparison technique of the present invention allows for more precise and accurate measurement of contamination than conventional methods of measuring the water directly. In addition, the present invention provides for more accurate contamination testing because the wafer rinsing process simulates conditions present in the manufacturing processes.

The present invention is not limited to use in determining contamination levels in rinsing fluid. The present invention could also be used to focus exclusively on the effects of the rinsing fluid on wafers. Alternatively, the present invention could be used to assist in evaluating different ion-exchange resins.

The present invention can also have application in the medical, pharmaceutical, biotechnological, food preparation, aerospace, and other processing industries where a portable clean area is necessary to test for contaminants or to protect objects from contamination.

The foregoing description of the preferred embodiments of the invention has been presented for purposes of illustration and description. It is not intended to be exhaustive or to limit the invention to the precise form disclosed, and many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A system for use in monitoring contamination of fluid received from a remote fluid source to rinse one or more crystal wafers, the system comprising:
   a portable framework including a chamber which encloses a workspace to isolate the workspace from an environment in which the system is located;
   a rinsing bath mounted within the chamber and configured to receive the one or more crystal wafers for rinsing, the rinsing bath having an input port which detachably connects to the remote fluid source to receive fluid for passage over the crystal wafers;
   a cassette configured to support the one or more crystal wafers in the rinsing bath;

a sealable container configured to receive the one or more crystal wafers after the one or more crystal wafers are rinsed so that the wafers may be transported from the chamber;

a transport structure mounted on the framework to accommodate transport of the system to and from the remote fluid source; and a wafer-quality measurement apparatus configured to test one or more characteristics of a rinsed crystal wafer for comparison with an optimal wafer, any difference in the one or more characteristics being indicative of contamination of the fluid received from the remote fluid source.

2. The system of claim 1 which further comprises a filter operatively mounted on the framework in communication with the chamber to filter air entering the workspace from the environment.

3. The system of claim 2, wherein the filter creates a vertical airflow within the workspace.

4. The system of claim 1, wherein the chamber defines an adjustable vent to the environment.

5. The system of claim 1, wherein the chamber defines a sealable portal between the workspace and the environment.

6. The system of claim 1, wherein the chamber is made of polypropylene.

7. The system of claim 1, wherein the rinsing bath includes an inner tank which holds wafers to be rinsed, and an outer tank which holds the inner tank, the input port being configured to introduce fluid from the remote fluid source into the inner tank for overflow into the outer tank.

8. The system of claim 7, wherein the outer tank has an output port for discharge of fluid received from the inner tank.

9. The system of claim 7, wherein the inner tank is made of quartz.

10. The system of claim 1, wherein the transport structure is a wheeled cart.

11. The system of claim 1, where the chamber includes a bottom and a drain positioned in the bottom so that fluid overflowing the rinsing bath flows to the bottom of the chamber and out the drain.

12. The system of claim 1, further comprising a flow meter associated with the input port to regulate the flow of fluid into the rinsing bath.

13. The system of claim 1, further comprising a shelf within the chamber configured to support the sealable container.

14. The system of claim 1, further comprising vents in the chamber configured to allow air to flow outwardly from the chamber.

15. The system of claim 1, further comprising a handle attached to the transport structure.

* * * * *